United States Patent [19]

Edwards

[11] Patent Number: 4,582,828
[45] Date of Patent: Apr. 15, 1986

[54] FUNGICIDAL 5-OXO-4-TRISUBSTITUTED TIN-1,3,4-OXADIAZOLINES

[75] Inventor: Laroy H. Edwards, Napa, Calif.

[73] Assignee: Chevron Research Company, San Francisco, Calif.

[21] Appl. No.: 661,513

[22] Filed: Oct. 16, 1984

[51] Int. Cl.$^4$ .................. A01N 55/04; C07F 7/22
[52] U.S. Cl. ........................... 514/189; 546/2; 548/101
[58] Field of Search ............ 546/2; 548/101; 514/189

[56] References Cited

U.S. PATENT DOCUMENTS

| | | | |
|---|---|---|---|
| 3,907,818 | 9/1975 | Buchel et al. | 548/101 |
| 4,061,491 | 12/1977 | Arndt et al. | 71/92 |
| 4,134,893 | 1/1979 | Yu | 548/144 |
| 4,486,424 | 12/1984 | Wehner et al. | 548/101 X |
| 4,499,098 | 2/1985 | Edwards | 514/364 |

FOREIGN PATENT DOCUMENTS 1434137 2/1966 France ................ 548/144

Primary Examiner—Donald G. Daus
Assistant Examiner—Diana G. Rivers
Attorney, Agent, or Firm—S. R. LaPaglia; T. G. DeJonghe; S. L. Biggs

[57] ABSTRACT

Compounds of the formula:

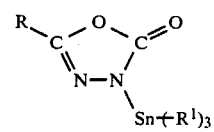

wherein R is aryl of 6 to 10 carbon atoms; substituted aryl substituted with 1 to 5 substituents selected from halogen, nitro, lower alkyl of 1 to 6 carbon atoms, lower alkoxy of 1 to 6 carbon atoms, lower alkylthio of 1 to 6 carbon atoms, trihalomethyl, or

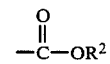

wherein $R^2$ is lower alkyl of 1 to 4 carbon atoms; alkyl of 1 to 8 carbon atoms; cycloalkyl of 3 to 8 carbon atoms; 1-alkylcycloalkyl of 4 to 9 carbon atoms; 1-alkylthio-1,1-dialkylmethyl of 4 to 7 carbon atoms; 1-alkoxy-1,1-dialkylmethyl of 4 to 7 carbon atoms; furyl; thienyl; or pyridyl; and $R^1$ is lower alkyl of 1 to 6 carbon atoms, cycloalkyl of 3 to 8 carbon atoms, aryl of 6 to 10 carbon atoms, substituted aryl of 6 to 10 carbon atoms substituted with 1 to 5 lower alkyl groups of 1 to 6 carbon atoms or aralkyl of 7 to 12 carbon atoms are fungicidal.

25 Claims, No Drawings

FUNGICIDAL 5-OXO-4-TRISUBSTITUTED TIN-1,3,4-OXADIAZOLINES

BACKGROUND OF THE INVENTION

The present invention relates to novel 5-oxo-4-trisubstituted tin-1,3,4-oxadiazolines which are fungicidal and in some cases insecticidal.

Certain 2-oxo-3-dialkoxyphosphoro-5-alkyl or cycloalkyl-1,3,4-oxadiazolines have been disclosed as insecticidal. See, e.g., U.S. Pat. Nos. 3,661,926 and 4,426,379.

SUMMARY OF THE INVENTION

The novel 5-oxo-4-trisubstituted tin-1,3,4-oxadiazolines of the present invention have the general formula:

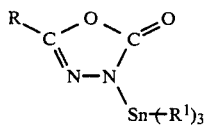
(I)

wherein R is aryl of 6 to 10 carbon atoms; substituted aryl substituted with 1 to 5 substituents selected from halogen, nitro, lower alkyl of 1 to 6 carbon atoms, lower alkoxy of 1 to 6 carbon atoms, lower alkylthio of 1 to 6 carbon atoms, trihalomethyl, or

wherein $R^2$ is lower alkyl of 1 to 4 carbon atoms; alkyl of 1 to 8 carbon atoms; cycloalkyl of 3 to 8 carbon atoms; 1-alkylcycloalkyl of 4 to 9 carbon atoms; 1-alkylthio-1,1-dialkylmethyl of 4 to 7 carbon atoms; 1-alkoxy-1,1-dialkylmethyl of 4 to 7 carbon atoms; furyl; thienyl; or pyridyl; and $R^1$ is lower alkyl of 1 to 6 carbon atoms, cycloalkyl of 3 to 8 carbon atoms, aryl of 6 to 10 carbon atoms, substituted aryl of 6 to 10 carbon atoms substituted with 1 to 5 lower alkyl groups of 1 to 6 carbon atoms or aralkyl of 7 to 12 carbon atoms.

Among other factors, the present invention is based on my surprising finding that the compounds of this invention are effective as fungicides and are particularly useful in controlling certain plant fungal diseases. In addition, some of the compounds of this invention show activity as insecticides and bactericides.

Preferred R groups include 1-alkylcycloalkyl, tertiary alkyl, aryl, furyl, and the like.

Preferred $R^1$ groups include aryl and cycloalkyl.

Particularly preferred R groups include 1-methylcyclopropyl, t-butyl, phenyl, and furyl.

Particularly preferred $R^1$ groups include phenyl and cyclohexyl.

DEFINITIONS

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group —(CH$_2$)$_m$— wherein m is an integer greater than zero. Typical alkylene groups include methylene, ethylene, propylene, and the like.

The term "alkoxy" refers to the group —OR' wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkoxyalkyl" refers to an alkyl group substituted with an alkoxy group. The term "lower alkoxyalkyl" refers to groups having up to a total of 8 carbon atoms and includes, for example, ethoxymethyl, methoxymethyl, 2-methoxypropyl, and the like.

The term "alkylthio" refers to the group —SR' wherein R' is an alkyl group. The term "lower alkylthio" refers to alkylthio groups having from 1 to 6 carbon atoms; examples include methylthio, ethylthio, n-hexylthio, n-propylthio, isopropylthio, isobutylthio, and the like.

The term "alkylthioalkyl" refers to an alkyl group substituted with an alkylthio group. The term "lower alkylthioalkyl" refers to groups having up to a total of 8 carbon atoms and includes, for example, ethylthiomethyl, methylthiomethyl, 2-methylthiopropyl, and the like.

The term "cycloalkyl" refers to cyclic alkyl groups. The term "lower cycloalkyl" refers to groups having from 3 to 6 carbon atoms in the ring, and includes cyclopropyl, cyclobutyl, cyclopentyl, and cyclohexyl.

The term "aryl" refers to aryl groups having from 6 to 10 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of 1 to 4 carbons substituted with an aryl group of from 6 to 10 carbons and includes, for example, benzyl, p-chlorobenzyl, p-methylbenzyl and 2-phenylethyl.

The term "1-alkoxy-1,1-dialkylmethyl" refers to the group

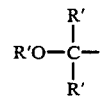

ps wherein R' is independently aryl.

The term "1-alkylthio-1,1-dialkylmethyl" refers to the group

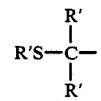

wherein R' is independently alkyl.

The term "alkylamino" refers to the group R'R"N— wherein R' is alkyl and R" is hydrogen or alkyl. The term "lower alkylamino" refers to alkylamino groups having 1 to 6 carbon atoms. Typical alkylamino groups include methylamino, ethylamino, diethylamino, dimethylamino, and the like.

The term "tertiary carbon" refers to the group

wherein R', R''' and R'''' are independently lower alkyl, or R''' is an alkoxy or alkylthio group, or R''' and R'''' taken together are an alkylene group, thus forming a cycloalkyl group.

The term "2-oxo-1,3,4-oxadiazolidine" refers to the

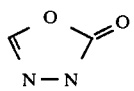

group. The conventional numbering system for this group is shown below:

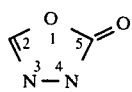

Pests are any insect, rodent, nematode, fungus, weed, or any form of terrestrial or aquatic plant or animal life or virus, bacterial organism or other microorganism (except those viruses, bacteria or other microorganisms existing in living humans or other living animals) considered injurious to health, the environment or man's economic well-being.

Pesticides are chemical entities or mixtures thereof intended for preventing, destroying, repelling or mitigating any pest.

The term "pesticide", when not specifically modified or delimited by other words, sometimes includes any one or a combination of the following: the active ingredient, the pesticide formulation or the pesticide product. It may also include baits for attracting and ultimately killing amphibian and reptile pests.

The terms "insecticide" and "insect" as used herein refer to their broad and commonly understood usages rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs such as spiders, mites, ticks, centipedes, worms, and the like.

DETAILED DESCRIPTION OF THE INVENTION

The compounds of the present invention may be conveniently prepared according to the following synthetic scheme:

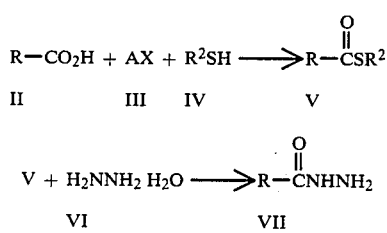

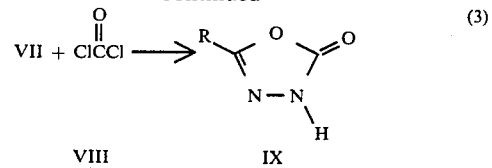

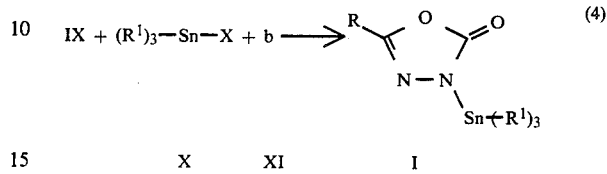

wherein R and $R^1$ are as previously defined in connection with formula I, $R^2$ is lower alkyl, AX is a halogenating agent, X is a halogen, and b is a base.

Reaction (1) is conducted by initially adding at about 0°–5° C. an essentially equimolar amount of a halogenating agent, III, to II. Any halogenating agent such as thionyl chloride, oxalyl chloride, and the like which is capable of converting a carboxylic acid to the corresponding acid halide may be used although thionyl chloride is preferred. The reaction is done in the liquid phase using an inert anhydrous organic solvent such as diethyl ether, chloroform, methylene chloride, and the like. After the addition, the system is then heated to reflux. Reaction pressure is not critical and for convenience the reaction is conducted at atmospheric pressure. After heating at reflux for from about 1 to 24 hours, the system is cooled to about 0°–5° C. An essentially equimolar amount of an alkyl mercaptan (IV), preferably ethyl mercaptan, is then added. The system is stirred at reflux for from about 1 to 24 hours and then at room temperature for an additional 1 to 48 hours. As noted before, reaction pressure is not critical at this step for convenience the reaction is conducted at atmospheric pressure. The product V is then isolated by conventional procedures such as extraction, filtration, chromatography, distillation or alternatively is used directly in reaction (2) without purification and/or isolation.

In reaction (2), the thioester, V, is added at about 0°–5° C. to approximately 1.5 equivalents of VI. The reaction is done in the liquid phase using a solution of alcohol and water as the solvent. Although various concentrations of alcohol to water may be used, the preferred solution is approximately 8:1 alcohol to water. The preferred alcohol in this reaction is methanol although other alcohols such as ethanol, isopropanol, and the like may be used. The reaction is conducted at a temperature of from about 0°–50° C. although preferably at from about 0°–5° C. Reaction pressure is not critical and for convenience the reaction is conducted at atmospheric pressure. The reaction is generally complete within about 1 to 48 hours. The product VII is then isolated by conventional procedures such as extraction, filtration, chromatography, distillation or alternatively is used directly in reaction (3) without purification and/or isolation.

Reaction (3) is conducted by adding approximately 0.6 to 1.1 equivalents of phosgene, VIII, to VII. The reaction is done in the liquid phase using an inert organic solvent such as methylene chloride, chloroform, toluene, and the like. Reaction pressure is not critical and for convenience the reaction is conducted at atmospheric pressure. After addition, the reaction is heated at reflux. Generally, the reaction is complete within about 1 to 20 hours. The product IX is then isolated by conventional procedures such as extraction, filtration, chromatography, distillation or alternatively is used directly in reaction (4) without purification and/or isolation.

Reaction (4) is conducted by combining approximately equimolar amounts of IX, X, and III in solvent. Although the reactants may be combined in any order, it is preferred to add XI in solvent to a mixture of IX and X in solvent. Suitable solvents include inert organic solvents such as methylene chloride, ether, dimethoxy ethane, and the like. The reaction is conducted at a temperature of about 0° C. to about 40° C., preferably from about 25° C. to about 40° C., or at reflux, and is generally complete within about 5 to about 12 hours. The product, I, is isolated by conventional procedures such as extraction, washing, stripping, filtration, and the like.

UTILITY

The compounds of the present invention are useful in controlling a wide variety of pests.

These compounds are active as fungicides and are particularly effective in controlling a variety fungi which are deleterious to plants, including plant fungal infections. These compounds are particularly effective in controlling leaf blights caused by organisms such as *Phytophthora infestans* and *Septoria apii*. In addition, some of these compounds are useful in controlling daily blights caused by organisms such as *Alternaria solani*, and powdery mildews such as that caused by *Erisiphe polygoni*. However, some of the compounds of this invention may be more fungicidally active than others against particular fungi.

In addition, some of the compounds of this invention show antibacterial activity and may inhibit bacterial growth.

Some of these compounds are also effective as insecticides and acaracides and may be used in controlling a variety of insect and arthropod pests. In particular, some of these compounds are especially effective as miticides. However, some of these compounds may be more insecticidally and acaricidally active than others against particular pests.

Like most insecticides, they are not usually applied full strength, but are generally incorporated with conventional biologically inert extenders or carriers normally employed for facilitating dispersion of active ingredients for agricultural chemical application, recognizing the accepted fact that the formulation and mode of application may affect the activity of a material. The toxicants of this invention may be applied as sprays, dusts, or granules to the insects, their environment or hostages susceptible to insect attack. They may be formulated as granules of large particle size, powdery dusts, wettable powders, emulsifiable concentrates, solutions, or as any of several other known types of formulations, depending on the desired mode of application.

Wettable powders are in the form of finely divided particles which disperse readily in water or other dispersants. These compositions normally contain from about 5% to 80% insecticide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the insecticidal composition.

Dusts are freely flowing admixtures of the active insecticide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the insecticide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for insecticidal applications include simple solutions of the active insecticide in a dispersant in which it is completely soluble at the desired concentration, such as acetone, alkylated naphthalenes, xylene, or other organic solvents. Granular formulations, wherein the insecticide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying insecticides are well known in the art.

The percentages by weight of the insecticide may vary according to the manner in which the composition is to be applied and the particular type of formulation, but in general comprise 0.5% to 95% of the toxicant by weight of the insecticidal composition.

The insecticidal compositions may be formulated and applied with other active ingredients, including nematocides, insecticides, fungicides, bactericides, plant-growth regulators, fertilizers, etc. In applying the chemical, an effective amount and concentration of the toxicant of this invention is, of course, employed.

The terms "insecticide" and "insect" as used herein refer to their broad and commonly understood usage rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs, such as spiders, mites, ticks, centipedes, worms, and the like.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

Example 1

Preparation of 1-Methylcyclothiopropanoic Acid Ethyl Ester 100 g of 1-methylcyclopropanoic acid was added to 150 ml of diethyl ether. The system was cooled to 0°–5° C. and 119 gm of thionyl chloride was added dropwise over a period of time. After addition, the system was heated at reflux for 8 hours. The system was then cooled to 0°–5° C. and 62 gm of ethanethiol was added dropwise. The system was heated at reflux for 6 hours and then stirred at room temperature for 72 hours. The diethyl ether was removed by stripping to give the 1-methylcyclopropanoic acid ethyl ester.

Example 2

Preparation of 2-(1'-Methylcyclopropyl)-5-Oxo-1,3,4-Oxadiazoline (a) 48 gm (approximately 1.5 equivalents) of hydrazine was first added to 80 ml of methanol and 12 ml of water was then added to the system. Afterwards, the 1-methylcyclopropanoic ethyl ester of Example 1 was added dropwise to the system at 0°–5° C. The system was then stirred overnight. The solvent was removed by stripping. The product was dissolved in methylene chloride and then dried over magnesium sulfate. The methylene chloride was removed by stripping to give 85 gm of 1-methylcyclopropane carboxylic acid hydrazide.

(b) 85 gm of 1-methylcyclopropane carboxylic acid hydrazide was added to methylene chloride on a 3-neck 2-liter round bottom flask. The system was first cooled to 0°–5° C. and 590.5 gm of a 12.5% solution of phosgene added dropwise over a period of time. The system was then heated at reflux for 7 hours. The methylene chloride was removed by stripping. The product was washed with petroleum ether and filtered to give 66.6 gm of 5-oxo-2-(1'-methylcyclopropyl)-1,3,4-oxadiazoline as light brown crystals, melting point 68°–70° C.

Example 3

Preparation of

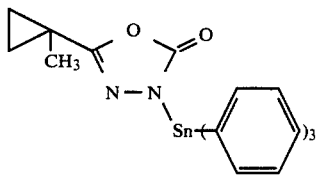

2-(1-Methylcyclopropyl)-4-Triphenylstannyl-5-Oxo-1,3,4-Oxadiazoline

To a stirred mixture of 5 g (0.035 mole) 2-(1'-methylcyclopropyl)-5-oxo-1,3,4-oxadiazoline and 13.5 g (0.035 mole) triphenyl tin chloride in methylene chloride (about 100 ml), 3.5 g (0.035 mole) triethylamine in methylene chloride (about 50 ml) was added dropwise. The reaction mixture was allowed to stir overnight at ambient temperature. The reaction mixture was refluxed (at about 40° C.) for about 3 hours, cooled and then allowed to stir at ambient temperature for about one hour. The reaction mixture was washed with water and then extracted with methylene chloride. The methylene chloride extract was dried and then stripped. The residue was washed with hexane to precipitate the above-identified product, melting point 165°–167° C.

Elemental analysis for $C_{24}H_{22}N_2O_2Sn$ showed: calculated %C 59, %H 4.5, and %N 5.7; found %C 55.48, %H 4.3, and %N 6.11.

Example 4

Preparation of

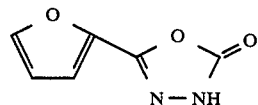

2-Phenyl-5-Oxo-1,3,4-Oxadiazoline

Into a stirred slurry of 25 g (0.18 mole) benzoylhydrazine in ethylacetate, 142.5 g (0.18 mole) 12.5% phosgene in toluene was dropped in. The reaction mixture was refluxed about 3 hours, and then allowed to stir over the weekend at ambient temperature. The flask was hooked to an aspirator and placed under vacuum to remove any possible peroxides. The mixture was filtered to give the above-identified product as a solid, melting point 133°–135° C.

Example 5

Preparation of

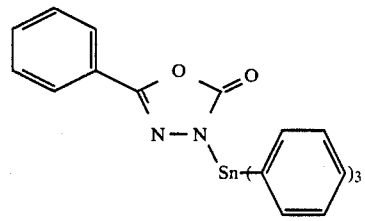

2-Phenyl-4-Triphenylstannyl-5-Oxo-Oxadiazoline

Into a stirred mixture of 3 g (0.02 mole) 2-phenyl-5-Oxo-1,3,4-oxadiazoline (the product of Example 4) and 7.7 g (0.02 mole) chlorotriphenyl tin in methylene chloride (about 100 ml), 2 g (0.02 mole) triethylamine in methylene chloride (about 50 ml) was dropped in. The reaction mixture was stirred overnight at ambient temperature, refluxed for 8 hours, and stirred overnight. The reaction mixture was washed with water and extracted with methylene chloride. The methylene chloride extract was dried and stripped to give the above-identified product as a solid, melting point 216°–218° C.

Elemental analysis for $C_{26}H_{20}N_2O_2Sn$ showed: calculated %C 61.1, %H 3.9, and %N 5.5; found %C 62.07, %H 4.24, and %N 5.52.

Example 6

Preparation of

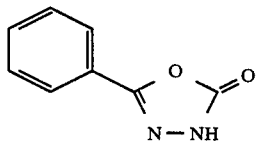

2-(2'-Furyl)-5-Oxo-1,3,4-Oxadiazoline

Into a stirred slurry of 25 g (0.2 mole) 2-furoic acid hydrazide in ethyl acetate, 158.3 g (0.2 mole) 12.5% phosgene in toluene was dropped in. The reaction mixture was stirred 1 hour, refluxed for about 2.5 hours, and stirred overnight. The reaction mixture was hooked up to an aspirator and placed under vacuum to remove any excess phosgene. The reaction mixture was filtered and stripped to remove ethyl acetate and toluene, yielding 30.3 g of the above-identified product as a solid, melting point 59°–63° C.

Example 7

Preparation of

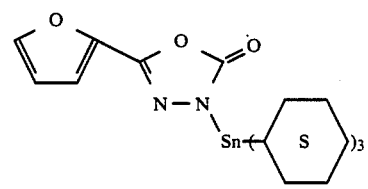

2-(2'-Furyl)-4-Tricyclohexylstannyl-5-Oxo-1,3,4-Oxadiazoline

Into a stirred mixture of 3 g (0.02 mole) 2-(2'-furyl)-5-oxo-1,3,4-oxadiazoline and 8 g (0.02 mole) tricyclohexyl tin chloride in methylene chloride, 2 g (0.02 mole) triethylamine in methylene chloride was dropped in. The reaction mixture was stirred about 1 hour at ambient temperature, refluxed about 4.5 hours, and stirred over the weekend. The reaction was refluxed about an additional hour, cooled and extracted with methylene chloride. The methylene chloride extracts were dried and stripped to give the above-identified product as a solid, melting point 159°–163° C.

Elemental analysis for $C_{24}H_{36}N_2O_2Sn$ showed: calculated %C 55.51, %H 7.0, and %N 5.4; found %C 55.64, %H 7.43, and %N 4.6

Compounds made in accordance with Examples 1 to 7 and using the appropriate starting materials are found in Table I.

In addition, by following the procedures disclosed in the Detailed Description of the Invention and in Examples 1 to 8 and using the appropriate starting materials, the following compounds are made:

2-(2'-thienyl)-4-(tri-n-butylstannyl)-5-oxo-1,3,4-oxadiazoline;
2-(2'-thienyl)-4-(tricyclohexylstannyl)-5-oxo-1,3,4-oxadiazoline;
2-(2'-thienyl)-4-(triphenylstannyl)-5-oxo-1,3,4-oxadiazoline;
2-(3'-pyridyl)-4-(tri-n-butylstannyl)-5-oxo-1,3,4-oxadiazoline;
2-(3'-pyridyl)-4-(tricyclohexylstannyl)-5-oxo-1,3,4-oxadiazoline;
2-(3'-pyridyl)-4-(triphenylstannyl)-5-oxo-1,3,4-oxadiazoline;
2-(tert-butyl)-4-(tri-n-butylstannyl)-5-oxo-1,3,4-oxadiazoline;
2-(tert-butyl)-4-(tricyclohexylstannyl)-5-oxo-1,3,4-oxadiazoline;
2-(tert-butyl)-4-(triphenylstannyl)-5-oxo-1,3,4-oxadiazoline;
2-(2'-chlorophenyl)-4-(tri-n-butylstannyl)-5-oxo-1,3,4-oxadiazoline;
2-(2'-chlorophenyl)-4-(tricyclohexylstannyl)-5-oxo-1,3,4-oxadiazoline;
2-(2'-chlorophenyl)-4-(triphenylstannyl)-5-oxo-1,3,4-oxadiazoline;
2-(4'-methoxyphenyl)-4-(tri-n-butylstannyl)-5-oxo-1,3,4-oxadiazoline;
2-(4'-methoxyphenyl)-4-(tricyclohexylstannyl)-5-oxo-1,3,4-oxadiazoline;
2-(4'-methoxyphenyl)-4-(triphenylstannyl)-5-oxo-1,3,4-oxadiazoline;
2-(1'-methylcyclohexyl)-4-(tri-n-butylstannyl)-5-oxo-1,3,4-oxadiazoline;
2-(1'-methylcyclohexyl)-4-(tricyclohexylstannyl)-5-oxo-1,3,4-oxadiazoline; and
2-(1'-methylcyclohexyl)-4-(triphenylstannyl)-5-oxo-1,3,4-oxadiazoline.

Example A

Bacterial Inhibition

Compounds of this invention were evaluated for in vitro bactericidal effectiveness by means of a bacterial inhibition test. This test is designed to measure the antibacterial activity of compounds in terms of degree of inhibition bacterial multiplication. The representative bacteria used were *Erwinia amylovora*, *Pseudomonas syringae* and *Xanthomonas vesicatoria*. Each compound to be tested was dissolved in acetone to give a 500 ppm concentration. Agar plates were inoculated using a micro sprayer with an suspension of the particular bacteria shortly (3 to 5 seconds) before treatment. The inoculated agar plates were then treated with the compound to be tested by spraying with a micro sprayer. The treated plates were incubated at 23.5° C. and the data was taken 24 hours after treatment. Antibacterial activities are measured by a zone of inhibited bacterial growth from the center of the agar plate and the deposit concentration in mg/cm² at the edge of the zone of inhibition ($ED_{99}$). The effectiveness of the compounds for antibacterial activity are reported in Table II in terms of the percent of the $ED_{99}$ of each compound of the $ED_{99}$ of the standard PMA (phenyl mercuric acetate).

Example B

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum*, *Rhizoctonia solani*, *Fusarium moniloforme*, *Botrytis cinerea*, *Aspergillus niger* and *Ustilago hordeii*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicidal activities are measured by a zone of inhibited mycelial growth from the center of the paper strip in terms of mg/cm² needed for 99½ control of the fungus ($ED_{99}$). The effectiveness of the compounds for fungicidal activity are reported in Table III in terms of the percent of the $ED_{99}$ of the test compound of the $ED_{99}$ of the standard Difolatan ®.

Example C

Tomato Late Blight

Compounds were tested for the preventative control of the Tomato Late Blight organism [Phytophthora infestans. Five- to six-week-old tomato (cultivar Bonny Best) seedlings were used. The tomato plants were sprayed with a 200-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table III.

Example D

Rice Blast

Compounds of this invention were tested for control of the Rice Blast organism [Piricularia oryzae, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table III.

Example E

Tomato Early Blight

Compounds were tested for the control of the Tomato Early Blight organism *Alternaria solani*. Tomato (variety Bonny Best) seedlings of 6- to 7-weeks old were used. The tomato plants were sprayed with a 200-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table III.

Example F

Celery Late Blight

The Celery Late Blight tests were conducted using celery (Utah) plants 11 weeks old. The Celery Late Blight organism was *Septoria apii*. The celery plants were sprayed with 200-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table III.

Example G

Bean Powdery Mildew

Compounds were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F; relative humidity was maintained at 40% to 60%. The percent disease control provided by a given test compound was based on the percent disease reduction relative to the untreated check plants. The results as percent control are tabulated in Table III.

Example H

Bean Rust

Compounds were evaluated for their ability to eradicate Bean Rust caused by *Uromyces phaseoli typica* on pinto beans.

Pinto bean plants, variety Idaho 1-11, 16 (summer) or 19 (winter) days old were inoculated with a 50-ppm suspension of uredospores in water containing a small amount of nonionic surfactant. The inoculated plants were placed in an environmental chamber immediately after inoculation and incubated 20 hours. Following the incubation period, the plants were removed from the chamber and placed in a greenhouse maintained at 66°-68° F. and 60-80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated Checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table III.

Example I

Aphid Control

The compounds of this invention were tested for their insecticidal activity against cotton aphids (*Aphis gossypii* Glover). An acetone solution of the test compound containing a small amount of nonionic emulsifier was diluted with water to give a concentration of 40 ppm. Cucumber leaves infested with cotton aphids were dipped in the test compound solution. Mortality readings were taken after 24 hours. The results are tabulated in Table IV in terms of percent control.

Example J

Aphid Systemic Evaluation

This procedure is used to assess the ability of a candidate insecticide to be absorbed through the plant root system and translocate to the foliage and thus to show insecticidal activity against the cotton aphid (*Aphis gossypii* Glover).

Two cucumber plants planted in a 4-inch fiber pot with a soil surface area of 80 cm$^2$ are used. Forty ml of an 80-ppm solution of the candidate insecticide is poured around the plants in each pot. (This corresponds to 40 gamma/cm$^2$ of actual toxicant). The plants are maintained throughout in a greenhouse at 75°-85° F. Forty-eight hours after the drenching, the treated plants are infested with aphids by placing well-colonized leaves over the treated leaves so as to allow the aphids to migrate easily from the inoculated leaf to the treated leaf. Three days after infestation, mortality readings were taken. The results are tabulated in Table IV in terms of percent control.

Example K

Mite Adult

Compounds of this invention were tested for their insecticidal activity against parathion-resistant Two-spotted Spider Mite [*Tetranychus urticae* Koch]. An acetone solution of the candidate toxicant containing a small amount of nonionic emulsifier was diluted with water to 40 ppm. Lima bean leaves which were infested with mites were dipped in the toxicant solution. The results are tabulated in Table IV in terms of percent control.

Example L

Mite Egg Control

Compounds of this invention were tested for their ovicidal activity against eggs of the two-spotted spider mite [*Tetranychus urticae* Koch]. An acetone solution of the test toxicant containing a small amount of nonionic emulsifier was diluted with water to give a concentration of 40 ppm. Two days before testing, 2-week old lima bean plants were infested with spider mites. Two days after infestation, leaves from the infested plants are dipped in the toxicant solution, placed in a petridish with filter paper and allowed to dry in the open dish at room temperature. The treated leaves were then held in covered dishes at about 31° C. to 33° C. for seven days. On the eighth day egg mortality readings are taken. The results, expressed as percent control, are tabulated in Table IV.

Example M

Housefly

Compounds of this invention were tested for their insecticidal activity against the Housefly (*Musca domestica* Linnaeus). A 500-ppm acetone solution of the candidate toxicant was placed in a micro sprayer (atomizer). A random mixture of anesthetized male and female flies was placed in a container and 55 mg of the above-described acetone solution was sprayed on them. A lid was placed on the container. A mortality reading was made after 24 hours. The results are tabulated in Table IV in terms of percent control.

Example N

American Cockroach

Compounds of this invention were tested for their insecticidal activity against Chlorodane-resistant American Cockroaches (*Periplaneta americana* Linnaeus). A 500-ppm acetone solution of the candidate toxicant was placed in a micro sprayer (atomizer). A random mixture of anesthethized male and female roaches was placed in a container and 55 mg of the above-described solution was sprayed on them. A lid was placed on the container. A mortality reading was made after 24 hours. The results are tabulated in Table IV in terms of percent control.

Example O

Alfalfa Weevil

The compounds of this invention were tested for their insecticidal activity against Alfalfa Weevil [*Hypera brunneipennis* (Boheman)]. A 500-ppm acetone solution of the candidate toxicant was placed in a micro sprayer (atomizer). A random mixture of male and female weevils was placed in a container and 55 mg of the above-described acetone solution was sprayed on them. A lid was placed on the container. A mortality reading was made after 24 hours. The results are tabulated in Table IV in terms of percent control.

Example P

Cabbage Looper Control

The compounds of this invention were tested for their insecticidal activity against Cabbage Looper [*Trichoplusia ni* (Hubner)]. An acetone solution of the candidate toxicant containing a small amount of nonionic emulsifier was diluted with water to give a concentration of 500 ppm. Excised cucumber leaves were dipped in the toxicant solution and allowed to dry. The leaves were then infested with Cabbage Looper larvae. Mortality readings were taken after 24 hours. The results are tabulated in Table IV in terms of percent control.

TABLE I

Compounds of the formula:

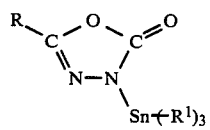

| | | | | ELEMENTAL ANALYSIS | | | | | |
|---|---|---|---|---|---|---|---|---|---|
| | | | | % C | | % H | | % N | |
| Compound | R | R¹ | Physical State | Calc. | Found | Calc. | Found | Calc. | Found |
| 1 44756 | ▷─CH₃ | —(CH₂)₃CH₃ | white solid, m.p. 80–83° C. | 50.37 | 50.32 | 7.98 | 8.1 | 6.53 | 6.63 |
| 2 44931 | ▷─CH₃ | ─⟨S⟩ | white solid, m.p. 148–150° C. | 56.82 | 53.95 | 7.95 | 8.00 | 5.52 | 6.13 |

TABLE I-continued

Compounds of the formula:

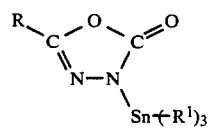

| Compound | R | R¹ | Physical State | %C Calc. | %C Found | %H Calc. | %H Found | %N Calc. | %N Found |
|---|---|---|---|---|---|---|---|---|---|
| 3 44809 | cyclopropyl-CH₃ | phenyl | white solid, m.p. 165–167° C. | 59.0 | 55.48 | 4.5 | 4.3 | 5.7 | 6.11 |
| 4 45040 | cyclopropyl-CH₃ | –CH₂–phenyl | white solid, m.p. 117–120° C. | 61.0 | 61.27 | 5.3 | 5.47 | — | — |
| 5 45182 | phenyl | cyclohexyl (S) | white solid, m.p. 188–190° C. | 59.01 | 60.5 | 7.2 | 7.65 | 5.3 | 5.37 |
| 6 45181 | phenyl | phenyl | white solid, m.p. 216–218° C. | 61.1 | 62.07 | 3.9 | 4.24 | 5.5 | 5.52 |
| 7 45186 | furyl | cyclohexyl (S) | white solid, m.p. 159–162° C. | 55.51 | 55.64 | 7.0 | 7.43 | 5.4 | 4.6 |
| 8 45185 | furyl | phenyl | white solid, m.p. 205–208°C. | 57.5 | 54 | 3.62 | 3.61 | 6.0 | — |

TABLE II

BACTERIAL INHIBITION

| Compound | Pseudo. | Erwin. | Xanth. |
|---|---|---|---|
| 1  44756 | 30 | 0 | 100 |
| 2  44931 | 0 | 0 | 31 |
| 3  44809 | 0 | 0 | 50 |
| 4  45040 | 26 | 0 | 100 |
| 5  45182 | 0 | 0 | 36 |
| 6  45181 | 0 | 0 | 53 |
| 7  45186 | 0 | 0 | 36 |
| 8  45185 | 0 | 0 | 75 |

Pseudo = *Pseudomonas syringae*
Erwin. = *Erwinia amylovora*
Xanth. = *Xanthomonas vesicatoria*

TABLE III

FUNGICIDAL ACTIVITY

Mycelial Inhibition

| Compound | Pyth. | Rhiz. | Fusar. | Botry. | Asper. | Ustil. | TLB | RB | TEB | CLB | BPM | BR |
|---|---|---|---|---|---|---|---|---|---|---|---|---|
| 1  44756 | 63 | 44 | 77 | 40 | 115 | 39 | 99 | 20 | — | 95 | 0 | 0 |
| 2  44931 | 0 | 0 | 0 | 0 | 51 | 46 | 94 | 20 | 100 | 99 | 100 | 0 |
| 3  44809 | 26 | 0 | 0 | 0 | 100 | 16 | 99 | 93 | 88 | 100 | 99 | 0 |
| 4  45040 | 0 | 0 | 0 | 0 | 0 | 0 | 44 | 13 | 0 | 81 | 0 | 0 |
| 5  45182 | 0 | 0 | 77 | 25 | 105 | 51 | 6 | 0 | — | 93 | 100 | 0 |
| 6  45181 | 45 | 30 | 87 | 38 | 175 | 40 | 98 | 36 | — | 100 | 100 | 0 |
| 7  45186 | 0 | 16 | 93 | 26 | 130 | 88 | 19 | 0 | — | 95 | 100 | 0 |

TABLE III-continued

FUNGICIDAL ACTIVITY

| Compound | | Mycelial Inhibition | | | | | | | | | | |
|---|---|---|---|---|---|---|---|---|---|---|---|---|
| | | Pyth. | Rhiz. | Fusar. | Botry. | Asper. | Ustil. | TLB | RB | TEB | CLB | BPM | BR |
| 8 | 45185 | 46 | 50 | 57 | 28 | 165 | 0 | 92 | 71 | — | 100 | 100 | 0 |

Pyth. = *Pythium ultimum*
GDM = Grape Downy Mildew
Rhiz. = *Rhizoctonia solani*
TLB = Tomato Late Blight
Fusar. = *Fusarium moniloforme*
RB = Rice Blast
Botry. = *Botrytis cineria*
TEB = Tomato Early Blight
Asper. = *Aspergillus niger*
CLB = Celery Late Blight
Ustil. = *Ustilago hordeii*
BPM = Bean Powdery Mildew
— = not tested or test failed
BR = Bean Rust

TABLE IV

INSECTICIDAL ACTIVITY

| Compound | | AR | AW | HF | MA | ME | Aph. | AS | CL | 5-CL |
|---|---|---|---|---|---|---|---|---|---|---|
| 1 | 44756 | 70 | — | 50 | 100 | 100 | 50 | 0 | 70 | 100 |
| 2 | 44931 | 0 | — | 0 | 90 | 70 | 0 | 0 | 70 | 100 |
| 3 | 44809 | 0 | — | 0 | 0 | 0 | 0 | 0 | 0 | 100 |
| 4 | 45040 | 0 | 0 | 0 | 0 | 0 | 0 | 0 | 60 | 100 |
| 5 | 45182 | 0 | — | — | 100 | 30 | 0 | 0 | 0 | 70 |
| 6 | 45181 | 0 | — | — | 0 | 0 | 20 | 0 | 0 | 100 |
| 7 | 45186 | 0 | — | — | 100 | 50 | 0 | 0 | 0 | 90 |
| 8 | 45185 | 0 | — | — | 0 | 0 | 0 | 0 | 0 | 70 |

AR = American Cockroach
AW = Alfalfa Weevil
HF = Housefly
MA = Mite Adult
ME = Mite Egg
Aph. = Aphid
AS = Aphid Systemic
CL = Cabbage Looper
5-CL = 5-Day Reading of Cabbage Looper Mortality
— = not tested or test failed

What is claimed is:

1. A compound of the formula:

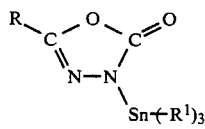

wherein R is aryl of 6 to 10 carbon atoms; substituted aryl substituted with 1 to 5 substituents selected from halogen, nitro, lower alkyl of 1 to 6 carbon atoms, lower alkoxy of 1 to 6 carbon atoms, lower alkylthio of 1 to 6 carbon atoms; trihalomethyl, or

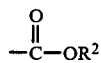

wherein $R^2$ is lower alkyl of 1 to 4 carbon atoms; alkyl of 1 to 8 carbon atoms; cycloalkyl of 3 to 8 carbon atoms; 1-alkylcycloalkyl of 4 to 9 carbon atoms; 1-alkylthio-1,1-dialkylmethyl of 4 to 7 carbon atoms; 1-alkoxy-1,1-dialkylmethyl of 4 to 7 carbon atoms; furyl; thienyl; or pyridyl; and $R^1$ is lower alkyl of 1 to 6 carbon atoms, cycloalkyl of 3 to 8 carbon atoms, aryl of 6 to 10 carbon atoms, substituted aryl of 6 to 10 carbon atoms substituted with 1 to 5 lower alkyl groups of 1 to 6 carbon atoms or aralkyl of 7 to 12 carbon atoms.

2. A compound according to claim 1 wherein R is aryl, substituted aryl, tertiary alkyl, cycloalkyl, 1-alkylcycloalkyl, 1-alkylthio-1,1-dialkylmethyl, 1-alkoxy-1,1-dialkylmethyl, furyl, or thienyl.

3. A compound according to claim 1 wherein R is aryl, substituted aryl, 1-alkylcycloalkyl, or furyl.

4. A compound according to claim 3 wherein R is aryl or 1-alkylcycloalkyl.

5. A compound according to claim 4 wherein R is 1-methylcyclopropyl.

6. A compound according to claim 5 wherein R is phenyl.

7. A compound according to claim 4 wherein R is tert-butyl.

8. A compound according to claim 4 wherein R is phenyl.

9. A compound according to claim 8 wherein $R^1$ is phenyl.

10. A compound according to claim 4 wherein R is furyl.

11. A compound according to claim 10 wherein $R^1$ is phenyl.

12. A compound according to claim 1 wherein R is 1-methylcyclopropyl, tert-butyl, phenyl, or furyl.

13. A compound according to claim 12 wherein $R^1$ is n-butyl, cyclohexyl, or phenyl.

14. A method of controlling fungi which comprises contacting said fungi or their growth environment with a fungicidally effective amount of a compound of claim 1.

15. A method of controlling fungi which comprises contacting said fungi or their growth environment with a fungicidally effective amount of a compound of claim 2.

16. A method of controlling fungi which comprises contacting said fungi or their growth environment with a fungicidally effective amount of a compound of claim 3.

17. A method of controlling fungi which comprises contacting said fungi or their growth environment with a fungicidally effective amount of a compound of claim 4.

18. A method of controlling fungi which comprises contacting said fungi or their growth environment with a fungicidally effective amount of a compound of claim 6.

19. A method of controlling fungi which comprises contacting said fungi or their growth environment with a fungicidally effective amount of a compound of claim 13.

20. A fungicidal composition which comprises an inert carrier and a fungicidally effective amount of a compound of claim 1.

21. A fungicidal composition which comprises an inert carrier and a fungicidally effective amount of a compound of claim 2.

22. A fungicidal composition which comprises an inert carrier and a fungicidally effective amount of a compound of claim 3.

23. A fungicidal composition which comprises an inert carrier and a fungicidally effective amount of a compound of claim 4.

24. A fungicidal composition which comprises an inert carrier and a fungicidally effective amount of a compound of claim 6.

25. A fungicidal composition which comprises an inert carrier and a fungicidally effective amount of a compound of claim 13.

* * * * *